(12) United States Patent
Irion

(10) Patent No.: US 6,269,693 B1
(45) Date of Patent: Aug. 7, 2001

(54) CAPACITIVE SENSOR FOR A FLUID FORMING A DIELECTRIC IN A CAPACITOR

(75) Inventor: Eckard Irion, Waldenbuch (DE)

(73) Assignee: DaimlerChrysler AG, Stuttgart (DE)

( * ) Notice: Subject to any disclaimer, the term of this patent is extended or adjusted under 35 U.S.C. 154(b) by 0 days.

(21) Appl. No.: 09/436,313

(22) Filed: Nov. 8, 1999

(30) Foreign Application Priority Data

Nov. 6, 1998 (DE) .............................. 198 51 213

(51) Int. Cl.[7] .......................... G01F 23/00; G01R 27/26; G08B 21/00
(52) U.S. Cl. ................. 73/304 C; 73/290 R; 324/665; 340/620
(58) Field of Search .............................. 73/304 C, 290 R; 324/665, 669; 340/620

(56) References Cited

U.S. PATENT DOCUMENTS

| | | |
|---|---|---|
| 4,128,857 | 12/1978 | Rayburn . |
| 4,562,733 | 1/1986 | Kant . |
| 5,423,214 | 6/1995 | Lee . |

FOREIGN PATENT DOCUMENTS

| | | |
|---|---|---|
| 1927694 | 11/1965 | (DE) . |
| 2048626 | 4/1982 | (GB) . |

Primary Examiner—Daniel S. Larkin
Assistant Examiner—Dennis Loo
(74) Attorney, Agent, or Firm—W. F. Fasse; W. G. Fasse

(57) ABSTRACT

A capacitive sensor for measuring a characteristic of a fluid or a filling depth of a liquid in a container is constructed of a printed circuit board that is either flexible or has stiff and flexible sections along its length. Metal coatings forming capacitor plates are formed, for example by printed circuit techniques on one or both sides of the circuit board which is then bent into such a configuration that two capacitor plates forming a capacitor face each other across a spacing that is accurately maintained by spacers. The bent shape of the circuit board has, for example, a U-configuration, an inverted S-configuration, or an e-configuration. Additional metal coatings are provided for screening purposes against adverse field influences. Conductor leads are provided on the printed circuit board for connecting the capacitor plates to an evaluating circuit, and the metal screens to a reference potential such as ground. The bent circuit board is held in position in a frame that itself may form a housing provided with openings for the inflow and outflow of the fluid which forms a dielectric between the capacitor forming plates. Lateral and vertical movement of the bent circuit board is further restrained by position fixing pins.

15 Claims, 2 Drawing Sheets

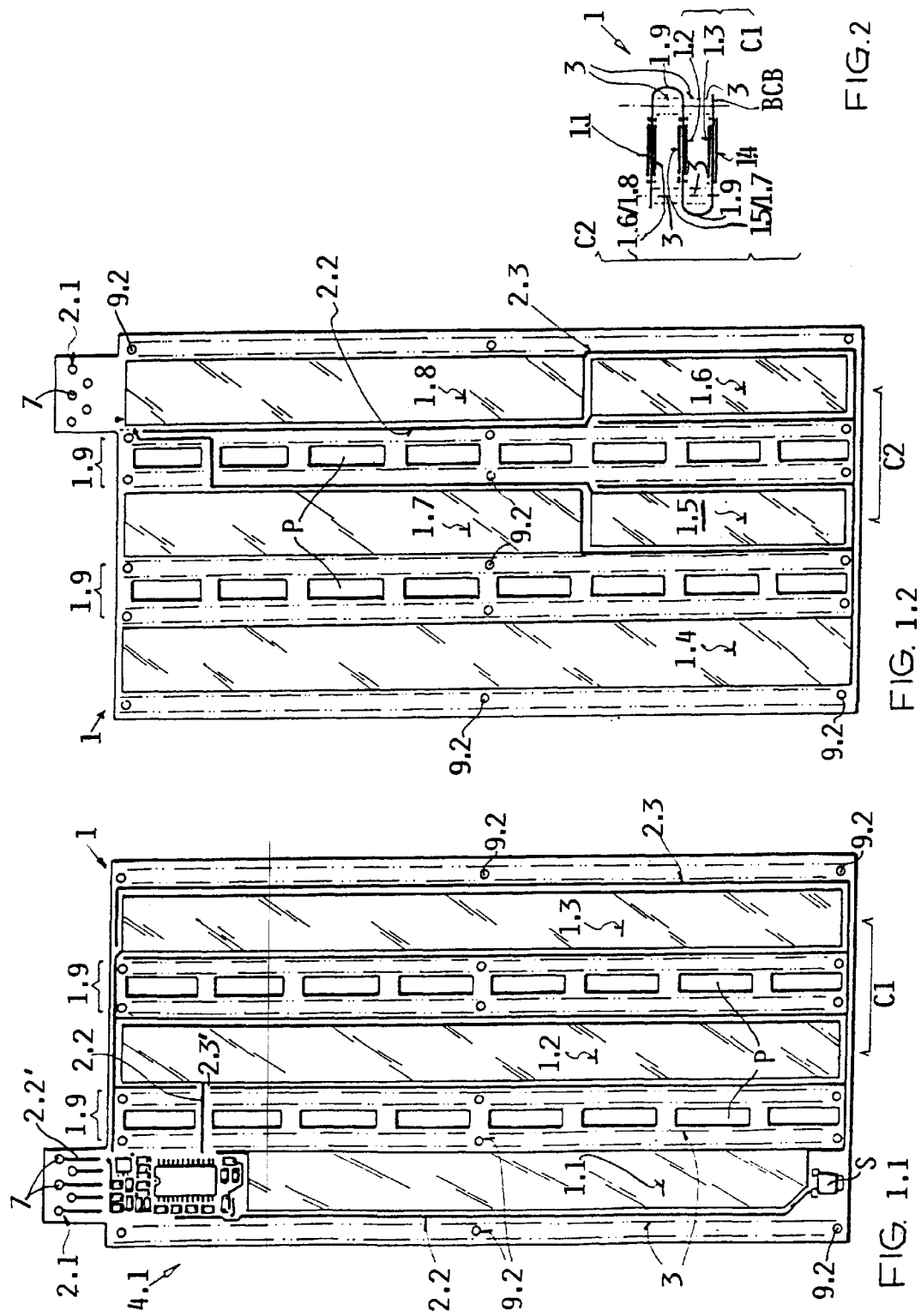

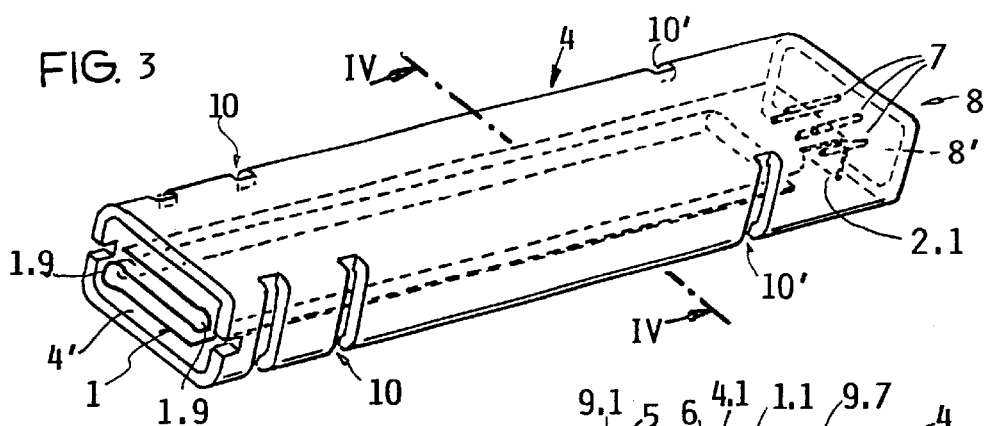
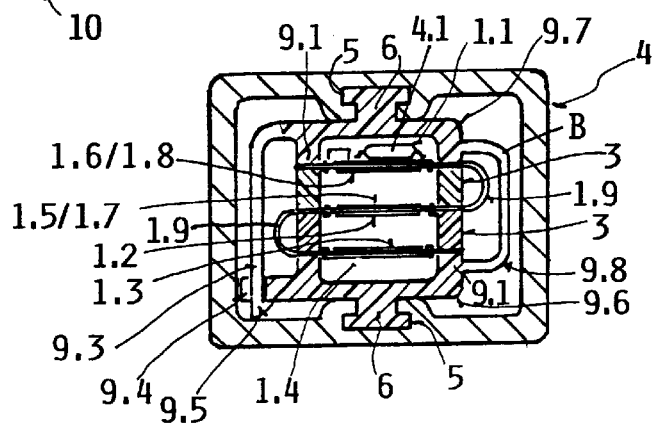
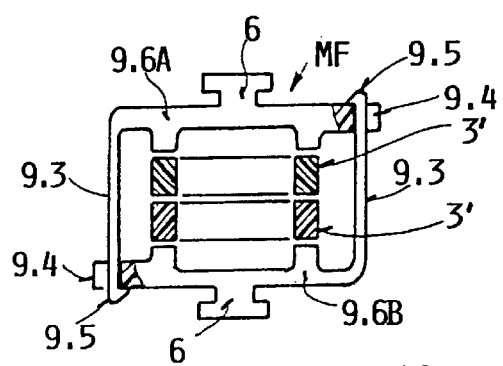
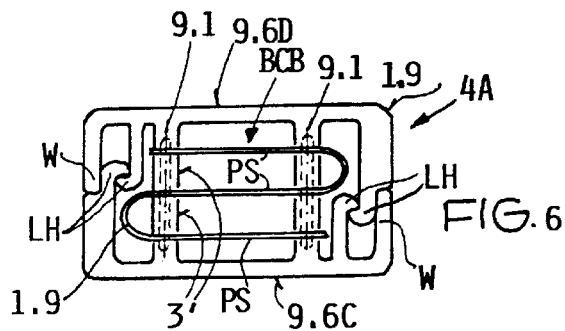
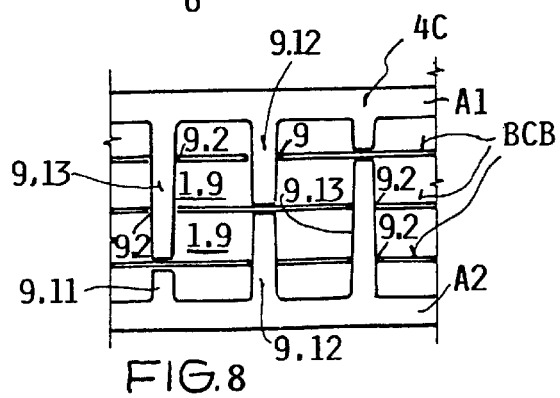
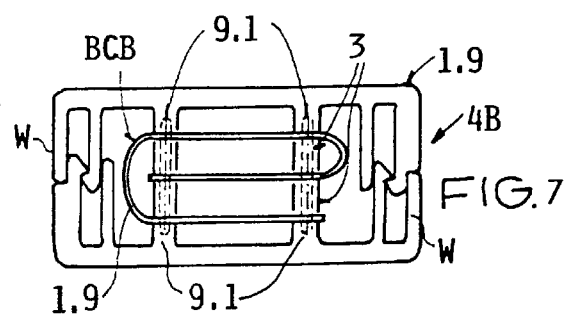

CAPACITIVE SENSOR FOR A FLUID FORMING A DIELECTRIC IN A CAPACITOR

This application is based on and claims the priority under 35 U.S.C. §119 of German Patent Application 198 51 213.9-35, filed on Nov. 6, 1998, the entire disclosure of which is incorporated herein by reference.

FIELD OF THE INVENTION

The invention relates to capacitive sensors in which a fluid, the characteristics of which are to be measured, forms a dielectric in one or more capacitors. The fluid may be a liquid or a gas that can enter into a hollow space between two capacitor plates.

BACKGROUND INFORMATION

Capacitive sensor devices according to the prior art are constructed as tubular capacitors or as plate capacitors.

German Utility Model Publication 19 27 694 (Bosch), published on Nov. 25, 1965, discloses an electrical capacitor with a folded sheet, tape or belt of insulating material carrying the capacitor plates or electrodes. The insulating material has metallized patterns that form the capacitor plates and conductor leads. The metallized patterns are all positioned on the same side of the tape or belt to permit a zig-zag folding pattern. Electrical connections are provided by metallized strips extending alongside the longitudinal edges of the tape or belt.

German Patent Publication DE 38 12 687 A1 (Normann et al.), published on Oct. 26, 1989 discloses a capacitive sensor for determining the filling level of a liquid in a container. Two electrodes 5 and 6 dip into the liquid. At least one of the two electrodes is provided with an electrically insulating cover layer. Two different frequencies are measured in order to ascertain the ohmic resistance and the capacitive resistance of the liquid between the electrodes. The respective signals are evaluated in a signal processing microcomputer for ascertaining the filling level as well as the water content in the liquid.

German Patent Publication DE 41 39 356 A1 (Brather), published on Jun. 3, 1993, discloses a plate capacitor for measuring of electric and dielectric characteristic values. Two covering electrodes (1) are spaced from each other. A central electrode (2) is positioned inside the space between the outer covering electrodes. The test samples to be measured are insertable into the spaces between the three electrodes.

Conventional measuring capacitors or capacitive sensors leave room for improvement especially with regard to their construction, more specifically, the ease of constructing and assemblying such capacitive sensors.

OBJECTS OF THE INVENTION

In view of the foregoing it is the aim of the invention to achieve the following objects singly or in combination:

to provide a capacitive sensor arrangement which is simple in its construction and assembly and hence can be competitively priced without sacrificing a relatively precise measurement;

to provide a measuring capacitor capable of ascertaining, for example the filling level in a container such as an oil container;

to provide a sensor probe which is rugged enough for use as an engine oil level sensor, such a sensor must assure an accurate spacing between capacitor plates even under adverse operating conditions inside an engine oil pan; and to construct the capacitor components in such a way that a unit is formed which can be repeatedly inserted and withdrawn from a protective housing.

SUMMARY OF THE INVENTION

According to the invention metal coatings are applied to an insulating elongated support member in the form of a printed circuit board that is flexible at least along spaced sections of the elongated support member. Metal coatings are applied to sections between the flexible sections to form capacitor plates or capacitor electrodes which are spaced from each other along the elongated support member by the flexible section or sections. At least one flexible section is bent to form at least one bend with a U-configuration, whereby the capacitor plates are brought into positions facing each other across a hollow space that is maintained in a dimensionally stable state by spacers between flat or plane legs of the U-bend in which the flexible section is a curved section after bending. The metal coatings that form the capacitor plates or electrodes are secured to these plane legs of the U-configuration. Conductor leads are also secured to the support member including the curved section thereof. The spacer or spacers are preferably provided with holes through which the medium to be measured can enter into the hollow space between the capacitor plates or through which the medium can flow to form a dielectric between the plates. After bending the support member is referred to as bent circuit board (BCB).

One or more capacitors may be formed in this fashion by repeatedly bending the flexible support member to form one or more bends. Various bending configurations may be employed, for example two U-bends facing in opposite directions may form an S-configuration or an e-configuration depending on the arrangement of the bends. In the simplest configuration there is one bend with two straight legs uniformly spaced from each other and held together by the curved flexible section. Where two bends are used, three straight legs are provided in such a way that a central leg is positioned between two outer leg, whereby the central leg will carry metal coatings on both sides to form two capacitor plates or electrodes.

Preferably, the central leg of the bent configuration is provided with a stiffener. However, the two metal coatings on opposite sides of the central leg may provide a sufficient stiffness where the support member is flexible along its entire length. A tape that has relatively stiff sections spaced along its length by relatively flexible sections is quite suitable for the present purposes. In all embodiments stiffer sections are connected by bendable flexible sections to form the required bent configurations.

In a preferred embodiment the bent configuration supporting the capacitor plates and the conductor leads is mounted in a frame, preferably a frame divided into two sections that can be snapped or pinned together. Such a frame is then preferably inserted into a protective housing providing a very rugged construction. The snap-in or pin connections fix the support member and the spacer or spacers in the required dimensionally stable position relative to each other. Moreover, the cover frame protects the sensor arrangement and permits the repeated insertion and withdrawal of the sensor into and out of the protective housing.

BRIEF DESCRIPTION OF THE DRAWINGS

In order that the invention may be clearly understood it will now be described in connection with example embodiments, with reference to the accompanying drawings, wherein:

FIG. 1.1 is a plan view of the front face of an at least partly flexible support member provided with metal coatings to form capacitor plates, electrical screens and conductor leads;

FIG. 1.2 is a plan view of the back face of the support member of FIG. 1;

FIG. 2 is an end view onto a support member bent into two oppositely facing U-configurations forming an inverted S-configuration with two curved sections interconnecting three straight sections;

FIG. 3 is a perspective view of a protective housing for the present sensors wherein the housing includes openings for the fluid to be measured;

FIG. 4 is a sectional view along section line IV—IV in FIG. 3 showing the bent configuration of FIG. 2 mounted in a frame inserted into the protective housing;

FIG. 5 shows an end view of a modified mounting frame having two separate sections that can be snapped together to form the frame into which spacers, shown in section, are inserted but without the sensor;

FIG. 6 shows another mounting frame having two sections that can be snapped together and that are further interlocked by position fixing pins;

FIG. 7 shows a mounting frame with a snap-in feature substantially as in FIG. 6 with position fixing pins and space for a bent configuration having an e-cross-section; and FIG. 8 is a view in a direction perpendicularly to the longitudinal axis of a protective mounting frame having fixed spacers of different lengths for holding the bent sensor configuration in the housing.

DETAILED DESCRIPTION OF PREFERRED EXAMPLE EMBODIMENTS AND OF THE BEST MODE OF THE INVENTION

The Figs. show a preferred embodiment of an elongated support member 1 made of electrically insulating material such as printed circuit board. After bending, as shown in FIG. 2, the bent circuit board BCB support carries at least one, preferably two, capacitors C1 and C2. The support member is bent into a curved configuration which includes at least one U-sectional form with one curved portion 1.9 extending into two plane sections or leg portions PS (FIG. 6). In a preferred embodiment the support member 1 is bent into an inverted S-configuration, see for example FIG. 6, or into an e-configuration shown in FIG. 7. The support member carries in addition to metallized coatings that form capacitor plates or capacitor electrodes, conductor leads and other metal or metallized coatings to form electrical screens against adverse field influences on the sensor. The inverted S-configuration and the e-configuration each includes two curved portions 1.9 and three straight or plane leg portions PS including two outer leg portions and an inner leg portion positioned between the outer leg portions as will be described in more detail below.

FIG. 1.1 shows a front face of the support member 1 while FIG. 1.2 shows the back face of the support member 1 prior to bending. The support member 1 carries on both sides metallized coatings. The coatings 1.2 and 1.3 are applied on the same side of the support member 1 and form respective capacitor plates for the first capacitor C1. The support member 1 carries on its opposite side two metal coatings 1.5 and 1.6 forming the second capacitor C2. The above-mentioned forming electrical screens are the metal coatings 1.1, 1.4, 1.7 and 1.8 carried by the support member 1. These electrical screens are connected to a reference potential for example to ground. The capacitor plates 1.5 and 1.6 have a smaller surface area than the capacitor plates 1.2 and 1.3. The smaller capacitor plates 1.5 and 1.6 are sufficient for determining the dielectric constant of the medium in the sensor. The rectangular configuration of the capacitor plates 1.5 and 1.6 can be modified, for example, square, triangular or other geometric configurations can be used. Conductor leads 2.2 are carried by the support member 1 and connect the capacitor plates to a signal evaluating circuit 4.1. Other conductor leads 2.2 connect the screen forming metal coatings to the reference potential. Still further conductor leads 2.2' connect the evaluating circuit 4.1 to a board extension 2.1 provided with plug-in elements 7 also shown in FIG. 3. Additional metallized strips 2.3 extend alongside, but insulated from the capacitor plates 1.2, 1.3, 1.5, 1.6. The additional metal strips 2.3 form lateral screens for protecting the capacitor plates. The lateral screens are either interrupted or bridged for the conductor leads 2.2. An interruption is shown at 2.3' in FIG. 1.1. A bridging may be provided on the opposite side of the support member 1. A conventional lead-through contact from one side of the support member 1 to the other side thereof may be provided for this bridging purpose. The support member 1 is normally provided with additional circuit components such as separate sensors for measuring the temperature or other parameters of the medium. Such additional sensor S is shown in FIG. 1.1. The sensor S is connected through a respective conductor lead 2.2 to the evaluating circuit 4.1.

As mentioned above, the support member 1 has relatively rigid plane sections or portions PS carrying the capacitor plates 1.2, 1.3 and 1.5, 1.6 and the screening metal coatings 1.1, 1.4, 1.7 and 1.8. These relatively rigid sections PS are spaced from each other by flexible bendable sections 1.9. The relatively rigid sections PS of the support section 1 may, for example, be thicker than the flexible sections 1.9. Alternatively, the flexibility of the sections 1.9 can be increased by providing perforations P as shown in FIGS. 1.1 and 1.2. Rather than making the rigid sections thicker, these sections may be part of a so-called "stiff-flex" tape or band along the length of which rigid sections PS alternate with flexible sections 1.9. Another possibility resides in providing the rigid sections with an additional stiffening member or members. Such stiffening members are particularly advantageous for the central stiff leg positioned between the two outer straight legs when the support member 1 is bent to have two curved sections 1.9 in the bent form BCB. Due to its central position, the central straight leg or portion forms the support for two metal coatings, one on each side. Thus, any stiffening if needed should be provided prior to bending.

Spacer members 3 are shown in dashed lines in FIGS. 1.1 and 1.2. These spacer members 3 make sure that once the support member 1 has been bent into the desired configuration BCB, the capacitor plates 1.2 and 1.3 of the first capacitor C1 and the capacitor plates 1.5 and 1.6 of the second capacitor C2 are maintained at a predetermined spacing from each other, respectively. As mentioned, the capacitor plates or electrodes need not necessarily have the shown rectangular elongated configuration. Other configurations may be suitable for different types of media to be measured. For example, triangularly shaped capacitor plates or trapezoidal shapes may be suitable.

FIG. 2 shows the support member 1 bent into an inverted S-configuration BCB with three straight leg sections PS (FIG. 6) and two curved sections or portions 1.9 interconnecting the straight sections PS. The capacitor plates 1.1 and 1.3 are secured to one side of the support member 1 and in the bent state of the support member 1, the plates 1.2 and 1.3 face each other across a fixed spacing forming with the plates the first capacitor C1. The capacitor plates 1.5 and 1.6 are arranged on the other side of the support member 1, but also face each other across a respective spacing to form the second capacitor C2. Metal coatings 1.1 and 1.4 are positioned on the outer straight leg portions PS and face outwardly for screening purposes to protect the sensor against external adverse field influences.

FIG. 3 shows one example embodiment of an outer protective housing for the present sensor. The housing 4 is provided with ports 10 for entry of the fluid into the measuring capacitors. Preferably, the housing 4 has an open end 4' for entry of the fluid into the housing and thus into the space between the capacitor electrodes 1.2, 1.3 and 1.5, 1.6. The other end of the housing 4 is provided with a connector section 8 forming a recess 8' in which the external support member section 2.1 is bent over so that contact pins 7 connected to conductor leads 2.2 shown in FIG. 1.1 reach into the recess or socket 8'. A plug-in cable, not shown, is provided with a respective plug-in end fitting into the socket 8' for power supply conductors and signal transmission conductors.

When the support member 1 with its capacitors C1, C2 is inserted into the housing 4, the entire unit can be submerged into the fluid in a container, whereby the fluid can enter into the housing and the capacitors through the open end 4' and through the ports 10. Any air contained in the capacitors can exit through the ports 10' at the upper end of the housing for pressure equalization inside the sensor and outside the sensor, whereby the filling level inside the sensor is the same as the filling level in a container into which the sensor is immersed. The open end 4' makes it possible to measure the depth of even a low level container content provided suitable conventional measuring methods are used for signal evaluation.

FIG. 4 illustrates an embodiment of a mounting frame 9.8 for holding the bent sensor configuration BCB and spacers 3 in the required fixed position relative to each other and for inserting the sensor with its mounting frame 9.8 into the housing 4. The mounting frame 9.8 comprises two members 9.6 and 9.7 interconnected on one side by a flexible bail B and on the opposite side by a snap-on latch 9.3 reaching into a cut-out 9.4 of the frame member 9.6 so that a hook 9.5 of the latch 9.3 can engage the lower frame member 9.6 while the other end of the latch 9.3 is secured to the upper frame member 9.7. Spacers 3 hold the plane circuit board sections in place in the frame 9.8. Each frame member 9.6 and 9.7 is provided with a guide tongue 6 that engages a respective guide groove 5 in the housing 4 when the mounting frame 9.8 is inserted longitudinally into the housing 4. FIG. 4 also shows the signal evaluating circuit 4.1 in an embedding material covered by the screen metal coating 1.

The spacers 3 are positioned outside the surface area of the capacitor plates 1.2 and 1.3 and 1.5, 1.6 and also outside of the metal coatings 1.4, 1.7 and 1.8. Position fixing pins 1.9 held in the frame members 9.6, 9.7 pass through holes 9.2 of the support member 1 and through the spacers 3, thereby fixing the position of the metal coatings against lateral and vertical displacement. Perforations P in the flexible portions 1.9 permit entry of the fluid into the spaces between the capacitor plates. Similarly, the perforations in cooperation with the holes 10, 10' in the housing 4 permit the fluid to flow through these spaces.

FIG. 5 shows another mounting frame MF for the bent circuit board BCB which itself is not shown in FIG. 5. The mounting frame of FIG. 5 also comprises two frame sections 9.6A and 9.6B of identical, but mirror-symmetrical construction. The spacer members 3' are provided in block form with additional openings for facilitating the inflow and outflow of the fluid as well as for pressure equalization to assure that the filling level in the sensor is equal to the filling level in a container. These additional openings may, for example, be positioned at the upper and lower end of the sensor arrangement. Position fixing pins 9.1 not shown in FIG. 5 may also be used in fixing the position of the spacers 3' and of the support member 1 against lateral and vertical displacement in the frame MF. The position fixing pins 9.1 are held in at least one of the frame members 9.6 or 9.7 in FIG. 4 or in 9.6A or 9.6B in FIG. 5.

It should be mentioned that the bail B shown in FIG. 4 has a certain reset spring force when it is bent open upon release of the latch hook 9.5. This reset spring force biases the latching elements 9.3, 9.4, 9.5 into a locked position, when the hook 9.5 engages the frame member 9.6 in FIG. 4. The same applies to the two flexible latches 9.3 in the frame MF of FIG. 5.

The above mentioned stiffening of the plane portions or sections PS of the support member 1, particularly for the central plane portion carrying the metal coatings 1.2, 1.5, and 1.7, are important particularly with regard to preventing the plane portions from sagging in response to gravity or to prevent their deformation particularly during assembly work.

FIG. 6 shows still another mounting frame 4A that may itself be a housing comprising mirror-symmetrical frame sections 9.6C and 9.6D cooperating with spacer members 3' and with position fixing pins 9.1 for fixing the bent circuit board BCB against horizontal and vertical displacements. The frame members 9.6C and 9.6D form half shells, each of which is equipped with two flexible snap-on latch hooks LH cooperating with the respective latch hook of the other half shell, whereby wall sections W back the engaged latch hooks LH to prevent unintended separation of the half shells from each other. The frame construction of FIG. 6 could be used as a protective housing 4A without insertion into a further housing as shown in FIG. 3. Electrical screening coatings may then be provided on the outer surfaces of the half shell sections 9.6C and 9.6D. Further, the half shell sections would be open ended and possibly provided with further openings as shown for the housing 4 in FIG. 3 to permit the entrance and exit of fluid to be measured and to further permit pressure equalization of the fluid inside the sensor and outside thereof.

FIG. 7 illustrates a further modification of a frame structure 4B made of two mirror-symmetrical half shells that could also function as a protective housing. Latch hooks LH function as in FIG. 6 and so do the wall sections W for preventing an unintended release of the latch hooks. The frame of FIG. 7 is particularly suitable for holding a BCB that was bent into an e-configuration, whereby the spacers 3' again cooperate with position fixing pins 9.1 to hold the e-configuration of the BCB against horizontal and vertical displacements.

FIG. 8 is a view in a direction perpendicularly to the longitudinal axis of a housing 4C having two sections A1 and A2 each provided with short position fixing spacers 9.11, intermediate or medium length position fixing spacers 9.12, and long position fixing spacers 9.13. In FIG. 8 the bent portions 1.9 of the bent circuit board BCB are seen, whereas the straight portions are positioned in front of the plane of the drawing toward the viewer. The long spacers 9.13 pass through holes 9.2 in the support member 1 but outside of the capacitor plates and other metal coatings. Similarly, the medium length spacers 9.12 pass through respective holes 9.2 in the bent circuit board BCB. The short spacers 9.11 provide a flat end surface against which the bent circuit board BCB can be held by an opposite flat end of the respective long spacer 9.13. The two intermediate length spacers 9.12 have flat ends that fix the position of the central plane section PS. Additional position fixing spacers 9.1 as shown, for example in FIG. 6, are not needed in FIG. 8 because the spacers of FIG. 8 assure with their shape and due to passing through the holes 9.2 that the bent circuit board BCB is properly held in a dimensionally stable position between the frame sections or half shells. As shown in FIG. 8, the arrangement of the spacers is such that the intermediate length spacer 9.12 of one housing half shell faces the respective intermediate length spacer of the other half shell. However, the short and long spacers 9.11 and 9.13 are positioned opposite each other to fix the respective outer plane sections PS of the BCB. The spacers 9.11, 9.12, 9.13 are positioned so that they do not interfere with the flow of the fluid to be measured through the sensor.

The diameter of the holes 9.2 in FIGS. 1.1, 1.2 and 8 will depend on the diameters of the respective spacers 9.11, 9.12, 9.13 that are to pass through these holes 9.2 thereby functioning also as locating pins for the bent circuit board.

Instead of providing the position fixing pins 9.1 in fixed positions in the frame sections and providing the spacers with through holes, it is also possible to secure the position fixing pins 9.1 to the spacers and provide respective holes in the frame sections to accommodate the free ends of the position fixing pins for the above mentioned horizontal and vertical securing of the BCB mounted in the frame. Where the pins 9.1 are held in the spacers the BCB is first folded around the spacers and secured thereto and thereafter the package is inserted on one half shell which is then engaged by a respective other half shell for closing the mounting frame.

Although the invention has been described with reference to specific example embodiments, it will be appreciated that it is intended to cover all modifications and equivalents within the scope of the appended claims. It should also be understood that the present disclosure includes all possible combinations of any individual features recited in any of the appended claims.

What is claimed is:

1. A capacitive sensor for measuring a characteristic of a fluid forming a dielectric between sensor capacitor plates, said capacitive sensor comprising a bent circuit board (BCB) having at least two plane sections (PS) and at least one flexible bent section (1.9) interconnecting said plane sections (PS) to form said bent circuit board (BCB) with at least one U-sectional configuration, metal coatings on said plane sections forming said capacitor plates (1.2, 1.3) facing each other across a fixed spacing to form a sensing capacitor (C1), spacer means (3) between said plane sections (PS) of said bent circuit board for maintaining said fixed spacing at a dimensionally stable thickness between said capacitor plates (1.2, 1.3), and flow port means in said sensor for said fluid to enter into said space between said capacitor plates and for venting said space.

2. The capacitive sensor of claim 1, wherein said bent circuit board (BCB) comprises at least two U-sectional configurations having open sides facing in opposite directions to form a sectional configuration having two outer plane sections (PS) and a single intermediate plane section (PS), two central capacitor plates (1.2, 1.5) on opposite sides of said intermediate plane section and two outer capacitor plates (1.6; 1.3) on inwardly facing sides of said bent circuit board (BCB) for forming at least two capacitors (C1, C2), and wherein said spacer means (3, 3') are so positioned that said dimensionally stable thickness is accurately maintained for both capacitors (C1, C2).

3. The capacitive sensor of claim 2, wherein said two U-sectional configurations form together an S-sectional configuration.

4. The capacitive sensor of claim 2, wherein said two U-sectional configurations form together an e-sectional configuration.

5. The capacitive sensor of claim 2, wherein said single intermediate plane section (PS) of said bent circuit board (BCB) comprises a stiffer characteristic than said bent sections (1.9) at least in an area where said two central capacitor plates (1.2, 1.5) are secured to said intermediate plane section (PS).

6. The capacitive sensor of claim 2, wherein said two outer plane sections and said intermediate plane section comprises a stiffer characteristic than said bent sections (1.9) at least in an area where said capacitor plates (1.2, 1.3; 1.5, 1.6) are secured to said plane sections (PS).

7. The capacitor sensor of claim 2, comprising on said bent circuit board (BCB) an electrical screen for protecting said sensor against adverse field influences.

8. The capacitor sensor of claim 7, wherein said electrical screen comprises further metal coatings (1.1 and 1.4) positioned on said two outer plane sections (PS), said metal coatings facing outwardly for protecting said sensor against adverse field influences, and conductor leads on said bent circuit board (BCB) connecting said further metal coatings (1.1, 1.4) to a reference potential.

9. The capacitive sensor of claim 7, wherein said electrical screen comprises metal strips (2, 3) laterally surrounding at least partly said capacitor plates (1.2, 1.3, 1.5, 1.6) for laterally screening said sensor against adverse field influences, and conductor leads on said bent circuit board (BCB) connecting said metal strips (2.3) to a reference potential.

10. The capacitive sensor of claim 2, further comprising a conductor lead connected to said two central capacitor plates (1.2, 1.5) on opposite sides of said intermediate plane section (PS) for connecting said two central capacitor plates (1.2, 1.5) to a common reference potential.

11. The capacitive sensor of claim 1, further comprising a mounting frame for said bent circuit board (BCB) and position fixing pins (9.1) in said mounting frame holding said spacer means (3, 3') and bent circuit board (BCB) against any displacement, said position fixing pins extending through holes (9.2) in said bent circuit board (BCB).

12. The capacitive sensor of claim 11, wherein said mounting frame comprises two half shells (9.6, 9.7) and interlatching means (9.3, 9.4, 9.5) for locking said half shells to each other with said bent circuit boards held in a fixed position between said half shells.

13. The capacitive sensor of claim 11, further comprising a protection housing (4) into which said mounting frame is insertable.

14. The capacitive sensor of claim 13, wherein said mounting frame and said protection housing (4) comprise guide means (5, 6) for guiding and holding said mounting frame when it is being inserted into said protection housing.

15. The capacitive sensor of claim 12, wherein each of said half shells comprises as said spacer means short position fixing spacers (9.11), medium length position fixing spacers (9.12) and long position fixing spacers (9.13) positioned in a stepped row in said half shells,
wherein said bent circuit board (BCB) comprises holes (9.2) through which said position fixing spacers extend for holding said bent circuit board (BCB) between said half shells.

* * * * *